US008431115B1

(12) United States Patent
Grimolfson

(10) Patent No.: US 8,431,115 B1
(45) Date of Patent: Apr. 30, 2013

(54) ANIMAL ATTRACTANT

(76) Inventor: Jeffrey Grimolfson, Houston, TX (US)

( * ) Notice: Subject to any disclaimer, the term of this patent is extended or adjusted under 35 U.S.C. 154(b) by 209 days.

(21) Appl. No.: 12/821,236

(22) Filed: Jun. 23, 2010

Related U.S. Application Data

(60) Provisional application No. 61/228,184, filed on Jul. 24, 2009.

(51) Int. Cl.
*A01N 25/00* (2006.01)
(52) U.S. Cl.
USPC .......................................................... 424/84
(58) Field of Classification Search .................. None
See application file for complete search history.

(56) References Cited

U.S. PATENT DOCUMENTS

| 6,165,570 | A | * | 12/2000 | Shannon | 428/34.1 |
| 6,572,903 | B1 | * | 6/2003 | Fuhr et al. | 426/73 |
| 2007/0095941 | A1 | * | 5/2007 | Gorres | 239/337 |
| 2008/0050411 | A1 | * | 2/2008 | Rudd | 424/410 |

* cited by examiner

*Primary Examiner* — Daniel Sullivan
*Assistant Examiner* — Melissa Javier
(74) *Attorney, Agent, or Firm* — Buskop Law Group, PC; Wendy Buskop

(57) ABSTRACT

An animal attractant composition comprising 35 weight percent to 45 weight percent of a primary mineral mixture, 35 weight percent to 45 weight percent of a cobalt iodized salt, 15 weight percent to 25 weight percent of a trace mineral and Vitamins A, B and E and a method for forming an artificial animal lick that lasts no less than 3 months.

8 Claims, No Drawings

ANIMAL ATTRACTANT

CROSS REFERENCE TO RELATED APPLICATION

The present application claims priority and the benefit of co-pending U.S. Provisional Application Ser. No. 61/228,184 filed on Jul. 24, 2009, entitled "ANIMAL ATTRACTANT". This reference is hereby incorporated in its entirety.

FIELD

The present embodiments generally relate to an animal attractant for use with hunting, which performs like an artificial mineral lick. The embodiments further relate to a method for creating an artificial animal lick, including bear bait, which needs no renewing for at least three months.

BACKGROUND

A need exists for a method for creating artificial animal licks to improve hunting conditions and a composition that can be used to create artificial animal licks.

A need exists for a composition and a method for creating a location with minerals and vitamins in an area where animals are without necessary vitamins to grow large and reproduce.

A need exists for a ready in the field composition for creating an animal lick, such as a deer lick that lasts at least three months.

The present embodiments meet these needs.

DETAILED DESCRIPTION OF THE EMBODIMENTS

Before explaining the present composition and method in detail, it is to be understood that the composition and method are not limited to the particular embodiments and that it can be practiced or carried out in various ways.

This animal attractant composition has a benefit that it provides vitamins in a mineral lick that lasts at least three months and is useful to help the animals stay healthy and grow bigger.

The animal attractant composition is used as a food supplement for various wild animals including bears, deer, moose, elk, and small mammals and is available continuously for at least 3 months.

The animal attractant composition is an easy to apply, pre-mixed composition enabling fast and direct application so that a hunter or wildlife manager does not have to use many ingredients and mix them together in the field, which is useful on a very cold or rainy day.

The composition is easy to store in its packaging, without needing certain temperature requirements. The composition can sustain heat extremes and cold extremes without degradation for at least 4 months.

The composition is easily transported in a bucket that can be reused by a hunter, enabling the animal attractant composition in the bucket to be a reusable assembly.

The animal attractant composition has the feature to work within less than 24 hours with typical wildlife mammals like possums, raccoons, and other small mammals of the like.

The present embodiments relate to a composition for an artificial animal lick that can be deployed in less than 5 minutes.

The animal attractant composition contains from 35 weight percent to 45 weight percent of a primary mineral mixture, from 35 weight percent to 45 weight percent of a cobalt iodized salt, and from 15 weight percent to 25 weight percent of a trace mineral mixture that requires no refrigeration to prevent spoilage. In particular, the animal attractant composition contains Vitamin B, Vitamin E and Vitamin A.

The primary mineral mixture can be made of a blend of calcium, phosphorous, magnesium, cobalt, Vitamin A, Vitamin B, and Vitamin E. Additionally, components of fluorine, iron, iodine, zinc, copper, cobalt, can be added to the mixture forming a food supplements for the mammals in the wild or even for domesticated animals.

The trace mineral mixture can be a combination of sodium, cobalt salt and zinc. Additionally, copper, manganese, and iodine can also be added to the trace mineral mixture.

The animal attractant composition includes from 5 weight percent to 10 weight percent molasses. The molasses can be powdered in an embodiment. In an embodiment, such as for bear bait, the molasses can be in liquid form.

In an embodiment, such as for bear bait, can include using an additional 1 weight percent to 7 weight percent anise oil with the molasses as well as 0.50 gallon of water to 1 gallon of the composition.

Still another embodiment includes using 2 weight percent to 4 weight percent of rolled oats. The rolled oats can be ground in an embodiment. The embodiment, such as the bear bait embodiment can use rolled oats.

For the bear bait embodiment, 1 weight percent to 2 weight percent of a beaver castor can be used in the form of a paste.

The bear bait embodiment can further include 1 weight percent to 2 weight percent of bread that can be ground into the composition of beaver castor, molasses, and anise with the primary mineral, cobalt iodized salt and trace minerals forming a goopy stiff mixture. The bread can be a whole loaf of old stale bread that is ground up and then poured into the mixer which can be a cement mixer.

Mixing occurs for a few minutes until the minerals are thoroughly mixed. For the bear bait embodiment the mixing can be from about 3 minutes to about 4 minutes until a goopy tar-like substance with a high viscosity is produced.

In addition to the animal attractant composition, the embodiments can include a method for forming an artificial mineral lick to attract wildlife or support the diet of domestic or wild mammals, which has as the steps, creating an animal attractant with 35 weight percent to 45 weight percent of a primary mineral, 35 weight percent to 45 weight percent of an iodized cobalt salt, and 15 weight percent to 25 weight percent of trace mineral that requires no refrigeration and ensuring the mixture has Vitamin A, Vitamin E and Vitamin B involved.

If the composition is to be used as bear bait, 0.50 gallon of liquid per 2 gallons of animal attractant composition can be used.

The animal attractant composition is formed by mixing the two mineral ingredients together along with the cobalt salt. The mixing of the ingredients should occur for from about 3 minutes to about 4 minutes using a cement mixer or tumbler.

In an embodiment, from about 10 gallons to 20 gallons of the animal attractant composition can be mixed at a time.

The mixture can be poured into 2 gallon buckets, which do not have to be airtight. The mineral mixture to form the animal lick has the feature of not needing to be airtight, although in about 4 months in a climate of 80 percent humidity, it can start to slightly congeal and should be repositioned into airtight containers.

The next step involves removing vegetation from an area of the ground. The ground is broken into small particulates, or fines.

Two gallons of animal attractant can be applied to the small particulates or fines.

Five gallons of water are applied to the animal attractant on the small particulates or fines However it can be noted that no water is added for the bear bait mixture embodiment other than the 0.50 gallon used to make the bear bait mixture.

The water can be mixed with the animal attractant composition by raking forming the artificial mineral lick. The artificial mineral lick lasts 3 months without reapplying the animal attractant composition.

The method can be used to create an artificial animal lick for use with moose, deer, elk, bears, horses, cows, wolves, coyotes, foxes, raccoons, opossums, rabbits, or grouse.

The method can include mixing the ingredients until a homogeneous mixture is created.

The method can also include creating the bear bait mixture by adding additional components to the animal attractant compositions and 0.50 gallon of water. Namely, to create the bear bait mixture, from 5 weight percent to 10 weight percent powdered molasses, from 1 weight percent to 7 weight percent anise oil, from 2 weight percent to 4 weight percent oats and from 1 weight percent to 2 weight percent beaver castor, such as in a paste form are added to the animal attractant composition.

The method can include adding 1 weight percent to 2 weight percent of ground bread to the mixture of primary mineral, trace mineral, molasses, anise oil, oats and beaver castor and then blending the mixture to form an goopy, tar-like substance for the bear bait embodiment.

In an embodiment, the animal attractant has no molasses or oils in it that the dry components are additionally ground to a coarse particulate.

In another embodiment, the primary mineral blend can include 14 weight percent to 18 weight percent calcium.

The primary mineral blend can have from 15 weight percent to 20 weight percent phosphorous.

The primary mineral blend can have from 1 weight percent to 8 weight percent magnesium.

The primary mineral blend can use 1900 mg to 2200 mg of fluorine.

The primary mineral blend can use 3300 mg to 3700 mg of iron.

The primary mineral blend can use from 73 mg to 77 mg iodine.

The primary mineral blend can use 7700 mg to 7900 mg zinc.

The primary mineral blend can use 2500 mg to 2700 mg copper.

The primary mineral blend can use 20 mg to 40 mg cobalt salt.

The primary mineral blend can include 460,000 IU/kg to 510,000 IU/kg of Vitamin A.

The primary mineral blend can use 49000 IU/kg to 51,000 IU/kg of Vitamin B.

The primary mineral blend includes 2400 IU/kg to 2600 IU/kg Vitamin E.

As an example, the trace mineral component can be from 80 weight percent to 98 we percent sodium salt.

The trace mineral component have from 7000 mg/kg to 12,000 mg/kg zinc and 2000 mg/kg to 7000 mg/kg copper. The trace mineral can have 6500 kg/mg to 9000 kg/mg manganese.

In an embodiment, from 30 mg/kg to 60 mg/kg cobalt can be used and from 120 mg/kg to 160 mg/kg iodine can be used.

The cobalt iodized salt can be 95 weight percent salt and include 37.5 weight percent sodium and 150 mg/kg cobalt.

While these embodiments have been described with emphasis on the embodiments, it should be understood that within the scope of the appended claims, the embodiments might be practiced other than as specifically described herein.

What is claimed is:

1. An animal attractant composition comprising 35 weight percent to 45 weight percent of a primary mineral blend, 35 weight percent to 45 weight percent of a cobalt iodized salt, and 15 weight percent to 25 weight percent of a trace mineral component, wherein the primary mineral blend comprises 14 weight percent to 18 weight percent calcium; 15 weight percent to 20 weight percent phosphorous; 1 weight percent to 8 weight percent magnesium; 1900 mg to 2200 mg of fluorine; 3300 mg to 3700 mg of iron; 73 mg to 77 mg iodine; 7700 mg to 7900 mg zinc; 2500 mg to 2700 mg copper; 20 mg to 40 mg cobalt salt; 460,000 IU/kg to 510,000 IU/kg of Vitamin A; 49000 IU/kg to 51,000 IU/kg of Vitamin B; and 2400 IU/kg to 2600 IU/kg Vitamin E, wherein the trace mineral component comprises 80 weight percent to 98 weight percent sodium salt; 7000 mg/kg to 12,000 mg/kg zinc; 2000 mg/kg to 7000 mg/kg copper; 6500 mg/kg to 9000 mg/kg manganese; 30 mg/kg to 60 mg/kg cobalt; and 120 mg/kg to 160 mg/kg iodine, and wherein the animal attractant composition requires no refrigeration.

2. The animal attractant composition of claim 1, further comprising 5 weight percent to 10 weight percent powdered molasses.

3. The animal attractant composition of claim 1, further comprising 1 weight percent to 7 weight percent anise oil.

4. The animal attractant composition of claim 1, further comprising 2 weight percent to 4 weight percent rolled oats.

5. The animal attractant composition of claim 1, further comprising 1 weight percent to 2 weight percent of a beaver castor.

6. The animal attractant composition of claim 5, wherein the beaver castor is in a paste form.

7. The animal attractant composition of claim 1, further comprising 1 weight percent to 2 weight percent of bread that is ground into the composition.

8. The animal attractant composition of claim 1, further comprising mixing 0.50 gallon of water into the animal attractant composition.

\* \* \* \* \*